United States Patent [19]

Ozawa et al.

[11] 4,267,360
[45] May 12, 1981

[54] NOVEL DERIVATIVES OF HEXAFLUOROPROPENE DIMER AND PROCESS FOR PREPARING SAME

[75] Inventors: Masahiro Ozawa, Kamifukuoka; Tadaaki Komatsu, Saitama; Kimiaki Matsuoka, Kawagoe, all of Japan

[73] Assignee: Central Glass Company, Limited, Ube, Japan

[21] Appl. No.: 84,854

[22] Filed: Oct. 15, 1979

Related U.S. Application Data

[63] Continuation of Ser. No. 825,476, Aug. 17, 1977, abandoned.

[30] Foreign Application Priority Data

Aug. 20, 1976 [JP] Japan .................................. 51-98747

[51] Int. Cl.$^3$ ...................... C07C 67/04; C07C 69/54; C07C 69/78
[52] U.S. Cl. .................................. 560/111; 560/223; 560/237; 560/64; 560/66; 560/185; 560/197; 560/262; 560/266; 260/410.9 R; 260/410.9 N
[58] Field of Search ................ 560/111, 223, 227, 64, 560/66, 87, 104, 105, 197, 229, 237, 262, 266; 568/843; 260/410.9 R

[56] References Cited

U.S. PATENT DOCUMENTS

3,419,602  12/1968  Pittman et al. .
3,823,171   7/1974  Pittman et al. .

OTHER PUBLICATIONS

Ishikawa, Nobuo et al., *Bulletin of the Chemical Society of Japan*, vol. 49 (2), pp. 502–505, (1976).
Yanagida, Shozo et al., *Tetrahedron Letters*, (27), pp. 2337–2340, (1977).
Yanagida, Shozo et al., *Tetrahedron Letters*, (33), pp. 2893–2894, (1977).
Martini, Thomas et al., *J. Fluorine Chemistry* (1976), pp. 535–540.

*Primary Examiner*—Natalie Trousof
*Assistant Examiner*—L. Hendriksen
*Attorney, Agent, or Firm*—Fleit & Jacobson

[57] ABSTRACT

Derivatives of hexafluoropropene dimer expressed by the following general formula

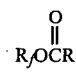

in which $R_f$ represents $(CF_3)_2C=C(CF_2CF_3)$ or $(CF_3)_2CH-CF(CF_2CF_3)$ and R represents a hydrocarbon residue of a carboxylic acid having one free site capable of reacting with the dimer. A process for preparing the derivatives is also disclosed in which the dimer is contacted with the carboxylic acid in an inert solvent in the presence of a catalyst. Metal, amine or ammonium salts of the acid may be also used for the reaction, in which case the reaction is feasible in the absence of a catalyst.

6 Claims, No Drawings

NOVEL DERIVATIVES OF HEXAFLUOROPROPENE DIMER AND PROCESS FOR PREPARING SAME

This is a continuation of application Ser. No. 825,476, filed Aug. 17, 1977, now abandoned.

This invention relates to novel derivatives of hexafluoropropene dimer and a process for preparing same.

It is known that hexafluoropropene is readily oligomerized in inert solvent in the presence of fluorine ions to give a dimer, a trimer or a mixture thereof. It is also known that the hexafluoropropene dimer, $(CF_3)_2C=CFCF_2CF_3$, serves as surface active agent by introduction with suitable hydrophilic groups such as carboxyl, sulfonyl, etc., or as water or oil repellent by introduction with polymerizable unsaturated groups by ether linkage. Further, reaction of the dimer with phenols in the presence of a tertiary amine catalyst is also known.

It is an object of the present invention to provide novel derivatives of hexafluoropropene dimer.

It is another object of the present invention to provide novel derivatives of hexafluoropropene dimer which are obtainable by reaction with carboxylic acids.

It is a further object of the present invention to provide novel derivatives of hexafluoropropene dimer which are excellent as water or oil repellent.

It is a still further object of the present invention to provide novel derivatives of hexafluoropropene dimer which are useful as intermediates copolymerizable with other monomers.

It is another object of the present invention to provide a process for preparing the derivatives of the type just mentioned.

The above objects can be achieved by derivatives of hexafluoropropene dimer expressed by the following formula

in which $R_f$ represents $(CF_3)_2C=C(CF_2CF_3)$ or $(CF_3)_2CH-CF(CF_2CF_3)$ and R represents a hydrocarbon residue of a carboxylic acid having one free site capable of reacting with the dimer.

The derivatives can be prepared by a process which comprises contacting the dimer with the carboxylic acid in an inert solvent in the presence of a catalyst selected from the group consisting of inorganic bases, tertiary amines and metal or amine salts of the same kind of the carboxylic acid used, or in the absence of the catalyst when a metal or amine or ammonium salt of the carboxylic acid is employed as reactant. That is, the reaction is conducted in the presence of the catalyst when free carboxylic acids are employed as reactant, or in the absence of a catalyst when the metal, amine or ammonium salt of the acid which also serves as catalyst for the reaction is employed as one of reactants.

The present invention will be described in detail.

Hexafluoropropene dimer or its preparation is well known and is not particularly described herein. Carboxylic acids which are employed for reaction with the dimer should have one free site capable of reacting with the dimer. Usable carboxylic acids are almost all of saturated or unsaturated aliphatic monocarboxylic acids, aromatic monocarboxylic acids with or without a substituent other than a hydroxyl group and a primary and a secondary amino groups which are active to the reaction of the invention. Specific examples of the monocarboxylic acids include saturated aliphatic monocarboxylic acids such as acetic acid, propionic acid, n-butyric acid, isobutyric acid, n-valeric acid, trimethylacetic acid, caproic acid, n-heptyric acid, caprylic acid, palargonic acid, and the like, unsaturated aliphatic monocarboxylic acids such as acrylic acid, methacrylic acid, crotonic acid, oleic acid, and the like, aromatic monocarboxylic acids such as benzoic acid, phenylacetic acid, hydrocinnamic acid, γ-phenylbutyric acid, δ-phenyl-n-valeric acid, ε-phenylcaproic acid, cinnamic acid, and the like. Specific halogenated monocarboxylic acids are also usable including monochloroacetic acid, monofluoroacetic acid, monobromoacetic acid, monoiodoacetic acid, α-chloropropionic acid), and β-chloropropionic acid. The aromatic monocarboxylic acids may have a substituent including an alkyl group containing from 1 to 20 carbon atoms, e.g., methyl, ethyl, etc., an ester, an amido group, a halogen, or an alkoxy group containing from 1 to 5 carbon atoms. Examples of such substituted aromatic acids are toluic acid, chlorobenzoic acid, bromobenzoic acid, methoxybenzoic acid, ethoxybenzoic acid, etc.

The carboxylic acids which have one free site reactive with the dimer may further include monoalkyl esters of aliphatic or aromatic dibasic acids, the monoalkyl moiety containing from 1 to 5 carbon atoms, such as monoalkyl succinate, e.g., methyl or ethyl succinate, monoalkyl adipate, e.g., methyl or ethyl adipate, etc., hydroxy acids the hydroxy group of which is esterified, such as compounds obtained by esterifying the hydroxy group of β-hydroxypropionic acid or hydroxybenzoic acid, e.g., anisic acid. Among the carboxylic acids just mentioned, acrylic acid, methacrylic acid and acetic acid are preferred.

In the practice of the invention, where free carboxylic acids are employed for reaction with the dimer, a catalyst is necessary as mentioned hereinbefore. Examples of the catalyst include inorganic bases such as sodium hydroxide, potassium hydroxide, potassium carbonate, tertiary amines such as trimethylamine, triethylamine, tri-n-propylamine. etc., metal or amine or ammonium salts of carboxylic acids. The metals useful for the above purpose are Na, K, etc. The amine salts are those of the tertiary amines mentioned above. When the metal salts, amine salts or ammonium salts of carboxylic acids are used as starting material for reaction with the dimer, any specific catalyst is not required. However, use of the salts is generally inferior in yield to the case using free carboxylic acids and catalysts. It will be noted that when the metal, amine or ammonium salt of the acid is used, the acid should preferably be the same as a starting carboxylic acid so as not to induce undesirable side reactions.

The reaction according to the invention is effected in solvent. Any organic solvents which are inert to the reaction system may be used. Preferably, ethers such as tetrahydrofuran, diethyl ether, glymes such as di, tri, tetraglymes, aproic polar solvents such as acetonitrile, sulforan, N,N-dimethylformamide, etc., are used. Hexafluoropropene dimer and the carboxylic acid should preferably be mixed for the reaction in equimolar quantities. As a metter of course, the dimer and the acid may be in any arbitrary mixing ratios but does not appear to offer any advantage. Accordingly, the equimolar quantities are conveniently employed. The amount of the catalyst may vary depending on the reaction temperature, the kinds of carboxylic acid, catalyst and solvent, and is generally in the range of not less than 1/100 mol, preferably 1/50 to 1/10 mole, of the employed carboxylic acid. Any concentrations of the reactants in the reaction system may be used and has no particular limitation. Temperatures above $-10°$ C. can be used for the reaction. Reaction temperatures between $-10°$ C. and $100°$ C. are practical. Atmospheric pressure is useful for the reaction though added or reduced pressure conditions may be usable. Reaction time is sufficient to be generally in the range of from 0.5 to 1 hour though it may vary depending on the reaction temperature, the kinds of carboxylic acid, catalyst and solvent.

The mechanism of the reaction is not understood completely at the present stage of our investigation. It is believed that the reaction proceeds through a carbanion intermediate as shown below:

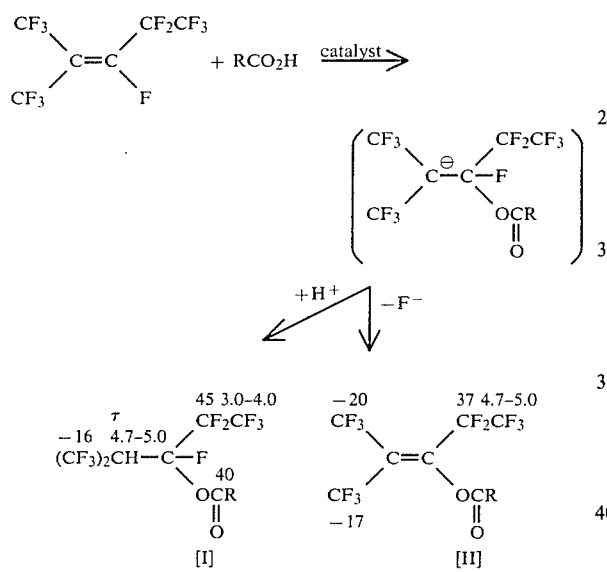

In the above reaction formulae (using free carboxylic acid), the numerical values at the respective carbon atoms are intended to imply chemical shifts for $^{19}F$ and $^1H$ expressed in terms of ppm and based on $CF_3COOH$ and tetramethylsilane (TMS), respectively. The ratio of products of formulae (I) and (II) may greatly vary depending on the kind of carboxylic acid. Use of acetic acid, acrylic acid or the like compounds which are hard to be susceptible to steric hindrance with regard to their carboxyl group will predominantly produce the compound of formula (I), whereas use of methacrylic acid, benzoic acid or the like compounds will give a mixture of the compounds of formulae (I) and (II). In addition, when carboxylic acid salts are used as starting material, the compound of formula (II) tend to be predominantly produced. Furthermore, if a proton source such as water is present in the reaction system, the addition product of formula (I) is obtained in large amount. While, the reaction in the absence of a proton source will yield a major proportion of a substitution product of formula (II). Aside from the products of formulae (I) and (II), there are sometimes obtained small amounts of by-products such as carboxylic anhydride, carboxylic acid fluoride, fluorine-contained ketone,

and an addition product of the dimer with hydrogen fluoride.

The derivatives of the dimer according to the invention are useful as water or oil repellent or, in some cases, intermediates for reaction with other copolymerizable monomers.

The present invention will be particularly illustrated by way of the following examples, in which products were identified by gaschromatography, an infrared analysis (using EPI, Model G-II, manufactured by Hitachi Seisakusho K. K.), an NMR analysis (using Models R-24A and R-24F, manufactured by Hitachi Seisakusho K. K.) and a mass spectrometry (using RMU Model 6MG, GC-Mass, manufactured by Hitachi Seisakusho K. K.). The products of formulae (I) and (II) could be readily identified since nuclear magnetic spectra for $^{19}F$ have the constant absorption peaks, regardless of the kind of carboxylic acid, as indicated in the foregoing reaction formulae. The NMR spectroscopy was conducted using a neat product or a mixture of products of formulae (I) and (II).

EXAMPLE 1

In a 20 cc round bottom flask equipped with a thermometer were placed 6 g (0.02 moles) of hexafluoropropene dimer, $(CF_3)_2C=CFCF_2CF_3$, 1.2 g (0.02 moles) of acetic acid and 10 cc of acetonitrile. To the mixture was dropwise added 0.1 g (0.001 mole) of triethylamine in about 5 minutes by use of a dropping funnel while agitating for reaction at room temperature by means of a magnetic stirrer. The reaction was continued for about 1 hour to obtain a uniform solution. The solution was then charged into iced water to obtain 6.05 g of an organic layer (at a yield of about 84.0% calculated as product of formula (I)). The organic layer was subjected to a gaschromatography, revealing that it contained the compound of formula (I) (wherein $R=CH_3$) with small amounts of $(CF_3)_2CHCF_2CF_2CF_3$,

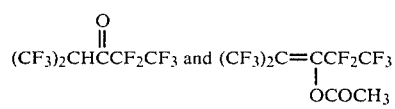

of formula (II).

The compound of formula (I) had the following boiling point and spectrum values,
Boiling point: 120°–123° C.
Infrared spectra: $v_{C=O}=1800$ cm$^{-1}$ (liquid) or 1810 cm$^{-1}$ (gas)
$^{19}F$-NMR spectra: $-16.0$ ppm (CF$_3$, 6F), 4.4 ppm (CF$_2$CF$_3$ 3F), 40.0 ppm (CF, 1F), 45.5 ppm (CF$_2$, 2F)
$^1H$-NMR spectra: $\tau 49.5$ ppm (H, 1H), $\tau 7.85$ ppm (CF$_3$, 3H)
Mass spectroscopy (M/e): 43 (CH$_3$CO, 100*), 60 (C$_2$H$_4$O$_2$, 10.3), 69 (CF$_3$, 7.6), 281 (C$_6$F$_{11}$, 3.7), 301 (C$_6$F$_{12}$H, 0.9), 360 (M, 0.002)

Note:
The value is intended to mean a relative intensity of peaks herein and whenever it appears hereinlater.

EXAMPLES 2-5

Example 1 was repeated using the reactants and solvents with or without use of catalyst as shown in Table 1 and reaction times of from 0.5 to 1.0 hours. The test results are shown in Table 1 below.

TABLE 1

| Example No. | Reactant (mole) | Catalyst (mole) | Solvent (10 cc) | Test Results |
|---|---|---|---|---|
| 2 | $CH_3CO_2Na$ (0.02) | — | N,N-dimethylformamide | mixture of compounds of formulae (I) and (II) |
| 3 | $CH_3CO_2Na \cdot 3H_2O$ (0.02) | — | acetonitrile | mixture of compounds of formulae (I) and (II) |
| 4 | $CH_3CO_2H$ (0.02) | $K_2CO_3$ (0.001) | acetonitrile | compound of formula (I) yield: 81.9% |
| 5 | $CH_3CO_2H$ (0.02) | $CH_3CO_2Na$ (0.001) | acetonitrile | compound of formula (II) yield: 94.6% |

EXAMPLE 6

Example 1 was repeated using 1.44 g (0.02 moles) of acrylic acid as carboxylic acid reactant, thereby obtaining 5.9 g of an organic layer. The organic layer was found to contain a compound of formula (I) (where R=CH=CH$_2$) with small amounts of the same by-products as indicated in Example 1. The yield of the compound was about 80%. The boiling point and the various spectrum values of the compound of formula (I) were as follows:

Boiling point: 41° C./15 mHg
Infrared spectrum ($\nu_{C=O}$): 1775 cm$^{-1}$ (liquid)
$^{19}$F-NMR spectra: −16.5 ppm (CF$_3$, 6F), 3.15 ppm (CF$_2$CF$_3$, 3F), 39.2 ppm (CF, 1F), 45.3 ppm (CF$_2$, 2F)
$^1$H-NMR spectra ($\tau$): 4.8 ppm (H, 1H), 3.1–4.1 ppm (CH=CH$_2$, 3H)
Mass spectrography (M/e): 55 (CH$_2$CHO, 100.0), 72 (C$_3$H$_4$O$_2$, 100.0), 72 (C$_3$H$_4$O$_2$, 68.0), 303 (M-69, 57.5), 27(CH$_2$=CH, 52.4), 281 (C$_6$F$_{11}$, 25.1), 69 (CF$_3$, 21.0), 372 (M, 10.2), 377 (M+1, 1.7)

The compound of formula (II) (where R=CH=CH$_2$) by-produced in small quantity had the following mass spectra (M/e): 55 (CH$_2$=CHCO, above 100), 27 (CH$_2$CH, 100), 56 (C$_3$H$_4$O, 21.3), 324 (M-28, 10.8), 69 (CF$_5$, 7.6), 119 (C$_2$F$_5$, 3.4), 333 (M-19, 2.9), 352 (M, 2.8)

EXAMPLE 7

Example 6 was repeated using as catalyst 0.001 mole of a triethylamine salt of acrylic acid. As a result, a compound of formula (I) (where R=CH=CH$_2$) was obtained at a yield of 90%.

EXAMPLE 8

Example 1 was repeated using 1.72 g (0.02 moles) of methacrylic acid, thereby obtaining 7.31 g of an organic layer. The organic layer was found to be a mixture of 84.4% by weight of a compound of formula (I) (where R=CH$_2$=CCH$_3$) and 15.6% by weight of a compound of formula (II) (where R=CH$_2$=CCH$_3$). The thus obtained compounds had the following spectrum values.

Compound of Formula (I) (where R=CH$_2$=CCH$_3$)

Infrared spectrum ($\nu_{C=O}$): 1778 cm$^{-1}$ (gas)
$^{19}$F-NMR spectra: −16.0 ppm (CF$_3$, 6F), 3.3 ppm (CF$_2$CF$_3$, 3F), 39.3 ppm (CF, 1F), 45.0 ppm (CF$_2$, 2F)
$^1$H-NMR spectra: $\tau$3.8 ppm (=CH$_2$, 1H), $\tau$42.5 ppm (=CH$_2$, 1H), $\tau$48.3 ppm (CH, 1H), $\tau$8.1 ppm (CH$_3$, 3H)
Mass spectra (M/e): 69 (C$_4$H$_5$O, CF$_3$, 100.0), 41 (CH$_2$=CHCH$_3$, 39.0), 386 (M, 17.1), 387 (M+1, 3.0)

Compound of formula (II) (where R=CH$_2$CCH$_3$)

Infrared spectrum ($\nu_{C=O}$): 1790 cm$^{-1}$ (gas)
$^{19}$F-NMR spectrum: −20.0 ppm (CF$_3$, 3F), −16.8 ppm (CF$_3$, 3F), 5.1 ppm (CF$_3$, 3F), 37.3 ppm (CF$_2$, 2F)
$^1$H-NMR spectra: The same values as of the compound of the formula (I).
Mass spectra (M/e): 69 (C$_4$H$_5$O, CF$_3$, 100.0), 41 (CH$_2$=CHCH$_3$, 54.3), 70 (C$_4$H$_6$O, 6.3), 347 (M-19, 0.6), 119 (C$_2$F$_5$, 0.5), 366 (M, 0.3)

EXAMPLE 9

Example 1 was repeated using 2.44 g (0.02 moles) of benzoic acid, thereby obtaining 8.7 g of an organic layer. The organic layer was subjected to a gas-chromatographic analysis and found to be a mixture of 6.6% of benzoic fluoride, 73.0% of a compound of formula (I) (where R=C$_6$H$_5$), and 20.4% of a compound of formula (II) (where R=C$_6$H$_5$) when calculated on the basis of the measured gaschromatographic areas). The compounds of formulae (I) and (II) had the following spectrum values, respectively.

Compound of formula (I) (where R=C$_6$H$_5$)

Infrared spectrum ($\nu_{C=O}$): 1765 cm$^{-1}$ (liquid)
$^{19}$F-NMR spectra: −16.3 ppm (CF$_3$, 6F), 3.0 ppm (CF$_2$CF$_3$, 3F), 38.9 ppm (CF, 1F), 44.8 ppm (CF$_2$, 2F)
$^1$H-NMR spectra: $\tau$2.0–2.2 ppm (phenyl radical, 2H), $\tau$2.53–2.8 ppm (phenyl radical, 3H), $\tau$4.67 ppm (CH, 1H)
Mass spectra (M/e): 105 (C$_3$H$_5$CO, 100.0), 77 (C$_6$H$_5$, 15.7), 106 (C$_7$H$_6$O, 14.4), 422 (M, 6.5), 122 (C$_7$H$_6$O$_2$, 4.8), 69 (CF$_3$, 1.8), 423 (M+1, 1.1)

Compound of formula (II) (where R=C$_6$H$_5$)

Infrared spectrum ($\nu_{C=O}$): 1780 cm$^{-1}$
$^{19}$F-NMR spectra: −20.4 ppm (CF$_3$, 3F), −17.2 ppm (CF$_3$, 3F), 4.7 ppm (CF$_3$, 3F), 37.0 ppm (CF$_2$, 2F)
$^1$H-NMR spectra: The same values as of the compound of formula (I).
Mass spectra (M/e): 105 (C$_6$H$_5$CO, 100.0), 77 (C$_6$H$_5$, 22.9), 106 (C$_7$H$_6$O, 8.4), 78 (C$_6$H$_6$, 1.9), 107 (C$_7$H$_7$O, 0.6) 383 (M-19, 0.5), 69 (CF$_3$, 0.5), 333 (M-69, 0.2), 402 (M, 0.1)

Application 3.72 g (0.01 mole) of the product

, $C_6F_{12}HOCCH=CH_2$, obtained in Example 6, 0.03 g (2 mole% of the above compound) of azoisobutyronitrile, and 5 g of $CF_2ClCFCl_2$ were placed in a tube and then hermetically sealed, followed by reacting at 70° C. for 6 hours in a shaker. As a result, a polymer was obtained. Then, a glass plate was immersed in a 1 wt% polymer solution in $CF_2ClCFCl_2$, withdrawn from the solution at a rate of 2 cm/minute, and air-dried. Thereafter, water droplet was placed on the polymer-coated plate to measure a contact angle, revealing that the contact angle was 109°. Thus, the polymer was found to have considerable water repellency. When paper and cloth sheets were each immersed in the above solution and dried, they exhibited remarkable water and oil repellency.

What is claimed is:

1. A process for preparing a mixture of compounds having the formula $$R_fOCR\overset{O}{\underset{\|}{}}$$

in which $R_f$ is $(CF_3)_2C=C(CF_2CF_3)$ in one compound of the mixture and $(CF_3)_2CH-CF(CF_2CF_3)$ in another compound of the mixture and R is a hydrocarbon residue of a monocarboxylic acid having the formula $RCO_2H$ selected from the group consisting of acetic acid, acrylic acid, methacrylic acid and benzoic acid, the process comprising contacting for reaction a hexafluoropropene dimer having the formula $(CF_3)_2=CFCF_2CF_3$ with said monocarboxylic acid in an inert solvent in the presence of a catalyst selected from the group consisting of inorganic bases, tertiary amines and sodium, potassium, amine and ammonium salts of the monocarboxylic acid used as reactant at a temperature between −10° C. and 100° C.

2. A process as claimed in claim 1, wherein the catalyst is used in an amount of not less than 1/100 mole of the employed carboxylic acid.

3. A process as claimed in claim 2, wherein the amount of the catalyst is in the range of from about 1/50 to 1/10 mole of the employed carboxylic acid.

4. A process as claimed in claim 1, wherein said dimer and said acid are used in equimolar quantities.

5. A process for preparing a mixture of compounds having the formula $$R_fOCR\overset{O}{\underset{\|}{}}$$

in which $R_f$ is $(CF_3)_2C=C(CF_2CF_3)$ in one compound of the mixture and $(CF_3)_2CH-CF(CF_2CF_3)$ in another compound of the mixture and R is a hydrocarbon residue of a monocarboxylic acid having the formula $RCO_2H$ selected from the group consisting of acetic acid, acrylic acid, methacrylic acid and benzoic acid, the process comprising contacting for reaction a hexafluropropene dimer having the formula $(CF_3)_2=CFCF_2CF_3$ with a self-catalytic reactant selected from the group consisting of sodium, potassium and amine salts of said monocarboxylic acid, at temperatures between −10° C. and 100° C.

6. A process as claimed in claim 5, wherein said dimer and reactant are used in equimolar quantities.

* * * * *